US006197314B1

(12) United States Patent
Einig

(10) Patent No.: US 6,197,314 B1
(45) Date of Patent: Mar. 6, 2001

(54) IMPEDING THE EXTRACTION OF ACTIVE INGREDIENTS OUT OF TABLETS

(75) Inventor: Heinz Einig, Neustadt (DE)

(73) Assignee: Warner Lambert Company, Morris Plains, NJ (US)

(*) Notice: Subject to any disclaimer, the term of this patent is extended or adjusted under 35 U.S.C. 154(b) by 0 days.

(21) Appl. No.: 09/156,538

(22) Filed: Sep. 17, 1998

(30) Foreign Application Priority Data

Sep. 18, 1997 (DE) .................................. 197 40 983

(51) Int. Cl.[7] .................................................. A61K 9/20
(52) U.S. Cl. ................. 424/400; 424/451; 424/456; 424/464; 424/474; 424/475; 424/477; 424/479
(58) Field of Search .................................. 424/400, 451, 424/456, 474, 475, 477

(56) References Cited

U.S. PATENT DOCUMENTS 3,169,092  2/1965  Petraglia et al. .

FOREIGN PATENT DOCUMENTS 9428870  12/1994  (WO) .
9608252   3/1996   (WO) .

OTHER PUBLICATIONS

The Physicians' Desk Reference, 52 Edition (Medical Economics Company 1998).*

* cited by examiner

Primary Examiner—Thurman K. Page
Assistant Examiner—P. E. McQueeney
(74) Attorney, Agent, or Firm—Evan J. Federman

(57) ABSTRACT

Solid oral administration forms from which the active ingredients can be isolated only with difficulty are described and comprise, besides conventional ingredients, as addition a mixture of pharmacologically suitable fats or gel formers with surfactants. Addition of the mixtures impedes extraction of the active ingredients out of the administration forms.

17 Claims, No Drawings

IMPEDING THE EXTRACTION OF ACTIVE INGREDIENTS OUT OF TABLETS

The present invention relates to oral administration forms from which the active ingredients can be isolated only with difficulty.

Amphetamines and ephedrones are dependency-forming drugs frequently used in the drug scene. The starting materials for preparing these substances are, inter alia, the active ingredients which are used in medicines for colds, racemic, (+)- and (−)-ephedrine, racemic, (+)- and (−)-pseudoephedrine and the corresponding phenylpropanolamines which are unsubstituted on the amino group. Since distribution of these substances is subject to strict international regulation and control, attempts are frequently made to isolate the starting materials from medicines and process them further to the corresponding drugs.

An aqueous solution of said active ingredients can easily be obtained from commercially available medicinal products, for example by comminution, acidic aqueous extraction and filtration, and they can be isolated therefrom by extraction with organic solvents after addition of alkali.

We have now found a way of making it possible to impede the isolation of said starting materials from medicines.

The present invention relates to solid oral pharmaceutical administration forms from which the active ingredients can be isolated only with difficulty, which comprise, besides conventional ingredients, as addition a mixture of pharmacologically suitable fats or gel formers with surfactants in an amount such that, when the forms are introduced into aqueous media, there is formation of a poorly filterable liquid which forms a creamy emulsion on extraction with organic solvents.

The present invention furthermore relates to the use of mixtures of pharmacologically suitable fats or gel formers with surfactants to impede the extraction of active ingredients out of solid oral pharmaceutical administration forms.

Active ingredients to be particularly considered are racemic ephedrine, (+)-ephedrine, (−)-ephedrine, racemic pseudoephedrine, (+)-pseudoephedrine and (−)-pseudoephedrine, and the corresponding phenylpropanolamines which are unsubstituted on the amino group, such as norephedrine and norpseudoephedrine. As a rule, the active ingredients are present in the medicines in the form of their salts with physiologically tolerated acids, in particular as hydrochlorides or sulfates.

Solid oral administration forms which may be mentioned are tablets, coated tablets (film- or sugar-coated tablets) and capsules (hard and soft gelatin capsules).

Pharmacologically suitable fats are: palm oil, hardened palm oil (P058), apricot kernel oil, cottonseed oil, carnauba wax, glycerol monostearate, mono- and diglycerides, cetyl alcohol, cetyl palmitate, hard fat USPXXII, coconut oil and arachis oil.

Pharmacologically suitable gel formers are xanthans, alginic acid and alkali metal alginates, gum arabic, agar, ghatti gum, karaya gum, tragacanth, guar gum, locust bean gum, pectin, chitin, amylopectin, gelatin, hydroxymethylpropylcellulose, methylcellulose, hydroxypropylcellulose, hydroxyethylcellulose, ethylcellulose, sodium carboxymethylcellulose, sodium carboxyethylcellulose, montmorillonite, polyacrylic acid and its methyl and ethyl esters, sodium carboxymethylstarch and sodium carboxyethylstarch. Pharmacologically suitable surfactants which may be mentioned are: sodium alkylsulfonates (RO—CO—CH$_2$—SO$_3$Na; R=C$_6$–Cl$_6$-alkyl radical), in particular sodium lauryl sulfoacetate; sodium laurylammonium sulfate, sodium lauryl sulfate, sodium dioctyl sulfosuccinate, s odium stearate, Aerosol® OT, glycerol monostearate, Span® 8.6HLB, Span® 4.7HLB, Arlacel® 20, 60, 80, 83, Tween® 20, 60, 80, Cremophor® O, Myrj® 45, 52, 59, poloxamer 188 (=Pluronic® F68), Cremophor® RH 40, 60, RH, EL, lecithin, lecithin S75-3 and S20-10. In the case of a tablet or coated tablet, the liquid and semisolid surfactants must before processing be processed with Aerosil® 200 to a solid and free-flowing composition.

The mixtures comprise the surfactants and fats in an amount such that, when the forms are introduced into aqueous media, there is formation of a poorly filterable liquid which forms a creamy emulsion on extraction with organic solvents. Suitable examples are mixtures which comprise the surfactants and fats in the ratio of from 95:1 to 1:95, preferably of (5 to 60):(40 to 90). A ratio of (20 to 60):(40 to 80) is particularly preferred.

The mixtures are incorporated into the administration forms in an amount such that their proportion relative to the amount of active ingredient in the administration form is from 1 to 300, preferably from 10 to 150 and, in particular, from 20 to 100%.

Addition of said mixtures to the administration forms impedes the isolation of the active ingredients out of the administration forms greatly and moreover considerably reduces the yield. The results on use of only the individual substances of the mixtures for this purpose are unserviceable.

The following examples show the possibilities for satisfactory use of the mixture.

EXAMPLES

1. Tablet production

The stated main ingredients (=M) were mixed, granulated with water, screened moist through a screen with a mesh width of 2 mm, dried in an oven at 40–50° C., rescreened through a screen with a mesh width of 1 mm, and mixed with the additives (=A). The granules were then tableted. The batch size was 0.5 kg. The mixtures and granules corresponded in their composition to the examples indicated below.

A. Example of a conventional instant release tablet without addition to prevent extraction:

| A. | Example of a conventional instant release tablet without addition to prevent extraction | |
|---|---|---|
| | M pseudoephedrine hydrochloride | 100 mg |
| | M lactose | 50 mg |
| | M microcrystalline cellulose | 32 mg |
| | M Kollidon ® 30 | 6 mg |
| | A Kollidon ® CL | 11 mg |
| | A magnesium stearate | 1 mg |
| B. | Example of a conventional instant release tablet with addition to prevent extraction: | |
| 1. | M pseudoephedrine hydrochloride | 100 mg |
| | M carboxymethylstarch, standard | 70 mg |
| | M sodium lauryl sulfate | 32 mg |
| | M lactose | 20 mg |
| | M Kollidon ® 30 | 15 mg |
| | A magnesium stearate | 2 mg |
| 2. | M phenylpropanolamine hydrochloride | 100 mg |
| | M carboxymethylstarch, standard | 70 mg |
| | M sodium lauryl sulfate | 32 mg |
| | M lactose | 20 mg |
| | M Kollidon ® 30 | 15 mg |
| | A magnesium stearate | 2 mg |

-continued

|     |                                      |        |
|-----|--------------------------------------|--------|
| 3.  | M (−)-ephedrine hydrochloride        | 100 mg |
|     | M carboxymethylstarch, standard      | 70 mg  |
|     | M sodium lauryl sulfate              | 32 mg  |
|     | M lactose                            | 20 mg  |
|     | M Kollidon ® 30                      | 15 mg  |
|     | A magnesium stearate                 | 1 mg   |
| 4.  | M pseudoephedrine hydrochloride      | 100 mg |
|     | M carboxymethylstarch, high-viscosity| 70 mg  |
|     | M sodium lauryl sulfate              | 32 mg  |
|     | M lactose                            | 20 mg  |
|     | M Kollidon ® 30                      | 15 mg  |
|     | A magnesium stearate                 | 2 mg   |
| 5.  | M pseudoephedrine hydrochloride      | 100 mg |
|     | M sodium alginate (150 cp)           | 10 mg  |
|     | M sodium lauryl sulfate              | 10 mg  |
|     | M Kollidon ® 30                      | 15 mg  |
|     | A microcrystalline cellulose         | 15 mg  |
|     | A magnesium stearate                 | 2 mg   |
| 6.  | M phenylpropanolamine hydrochloride  | 100 mg |
|     | M sodium alginate (150 cp)           | 10 mg  |
|     | M sodium lauryl sulfate              | 10 mg  |
|     | M Kollidon ® 30                      | 15 mg  |
|     | A microcrystalline cellulose         | 15 mg  |
|     | A magnesium stearate                 | 2 mg   |
| 7.  | M pseudoephedrine hydrochloride      | 100 mg |
|     | M methocel E4M                       | 40 mg  |
|     | M sodium lauryl sulfate              | 10 mg  |
|     | M lactose                            | 30 mg  |
|     | M microcrystalline cellulose         | 10 mg  |
|     | M Kollidon ® 30                      | 15 mg  |
|     | A magnesium stearate                 | 2 mg   |
| 8.  | M pseudoephedrine hydrochloride      | 60 mg  |
|     | M methylcellulose                    | 20 mg  |
|     | M poloxamer 188                      | 10 mg  |
|     | M lactose                            | 42 mg  |
|     | M corn starch                        | 30 mg  |
|     | M microcrystalline cellulose         | 20 mg  |
|     | M Kollidon ® 30                      | 15 mg  |
|     | A Kollidon ® CL                      | 15 mg  |
|     | A magnesium stearate                 | 2 mg   |
| 9.  | M (−)-ephedrine hydrochloride        | 60 mg  |
|     | M palm fat, PO 58                    | 30 mg  |
|     | M lecithin (S20-10)                  | 10 mg  |
|     | M lactose                            | 40 mg  |
|     | M corn starch                        | 30 mg  |
|     | M microcrystalline cellulose         | 18 mg  |
|     | M Kollidon ® 30                      | 8 mg   |
|     | A Kollidon ® CL                      | 10 mg  |
|     | A magnesium stearate                 | 2 mg   |
| 10. | M phenylpropanolamine hydrochloride  | 60 mg  |
|     | M palm fat, PO 58                    | 30 mg  |
|     | M lecithin (S20-10)                  | 10 mg  |
|     | M lactose                            | 40 mg  |
|     | M corn starch                        | 30 mg  |
|     | M microcrystalline cellulose         | 8 mg   |
|     | M Kollidon ® 30                      | 8 mg   |
|     | A Kollidon ® CL                      | 10 mg  |
|     | A magnesium stearate                 | 2 mg   |
| 11. | M pseudoephedrine hydrochloride      | 60 mg  |
|     | M methylcellulose                    | 18 mg  |
|     | M palm fat                           | 18 mg  |
|     | M lecithin                           | 6 mg   |
|     | M corn starch                        | 30 mg  |
|     | M microcrystalline cellulose         | 18 mg  |
|     | M Kollidon ® 30                      | 8 mg   |
|     | A Kollidon ® CL                      | 10 mg  |
|     | A magnesium stearate                 | 2 mg   |

The tablets can be coated with polymers in a known manner to give film-coated tablets or be further processed with sugar mixtures to give sugar-coated tablets in a known manner.

In place of the tablets obtained in this way, it is also possible to produce hard gelatin capsules by filling two-piece gelatin capsules with the granules.

C. Tablet production by direct tableting

All the tablet ingredients were mixed together in one step and compressed to tablets. The batch size was 0.5 kg. The mixtures corresponded in their composition to the examples indicated below.

|    |                                  |       |
|----|----------------------------------|-------|
| 1. | pseudoephedrine hydrochloride DTP| 63 mg |
|    | methylcellulose                  | 35 mg |
|    | poloxamer 188                    | 18 mg |
|    | lactose                          | 6 mg  |
|    | microcrystalline cellulose       | 18 mg |
|    | AcDiSol                          | 6 mg  |
|    | Kollidon ® 30                    | 8 mg  |
|    | magnesium stearate               | 2 mg  |
| 2. | pseudoephedrine hydrochloride DTP| 63 mg |
|    | methylcellulose                  | 15 mg |
|    | palm fat                         | 18 mg |
|    | lecithin (S20-10)                | 20 mg |
|    | microcrystalline cellulose       | 14 mg |
|    | Kollidon ® 30                    | 7 mg  |
|    | magnesium stearate               | 1 mg  |

Pseudoephedrine hydrochloride DTP comprises granules with an active ingredient content of 95% produced as disclosed in PCT/EP/97/03598.

D. Production of soft gelatin capsules

Soft gelatin capsules each comprising a mixture of 60 mg of pseudoephedrine hydrochloride, 180 mg of arachis oil, 60 mg of hydroxypropylcellulose and 20 mg of sodium lauryl sulfate were produced. The batch size was 0.5 kg.

The tablets and capsules obtained in these ways were tested for active ingredient release as follows:

In each case, one tablet was dissolved in 100 ml of water at pH 1–2. After heating and lengthy standing, the undissolved ingredients were removed and the solution, if a solution had been obtained after filtration, was mixed with 100 ml of dichloromethane and vigorously shaken or stirred until two phases had formed. The active ingredient content in the organic phase was then determined by photometry. If there was no clear separation of the phases, the active ingredient content in larger oil droplets was determined.

The following amounts of active ingredient were determined in the organic phase using the formulas described above:

| Example A              | 95% |
|------------------------|-----|
| (comparative example): |     |
| Example B-1            | 25% |
| Example B-2            | 23% |
| Example B-3            | 24% |
| Example B-4            | 30% |
| Example B-5            | 28% |
| Example B-6            | 23% |
| Example B-7            | 6%  |
| Example B-8            | 4%  |
| Example B-9            | 3%  |
| Example B-10           | 4%  |
| Example B-11           | 5%  |
| Example C-1            | 8%  |
| Example C-2            | 2%  |
| Example D              | 5%  |

However, in practice, considerably larger amounts of tablets are employed for each amount of water. It is therefore possible in practice to extract an even smaller percentage of active ingredient than in the indicated examples.

What is claimed is:

1. A solid oral administration form comprising a pharmacologically active ingredient homogeneously blended with an extraction-preventing composition, said extraction-preventing composition consisting essentially of a surfactant, and a fat or gel former in a weight ratio of from 95:1 to 1:95, wherein said extraction-preventing composition is blended with said pharmacologically active ingredient in an amount of 1–300:1, such that said solid oral administration form produces a creamy emulsion on extraction with organic solvent whereby no more than 30 percent of said active ingredient is contained in said organic solvent;

said surfactant being an alkylsulfonate compound according to the formula RO—CO—CH$_2$—SO$_3$Na wherein R=C$_{6-16}$ alkyl;

said fat being selected from the group consisting of palm oil, hardened palm oil, apricot kernel oil, cottonseed oil, carnauba wax, glycerol monosteorate, monoglyceride, diglyceride, cetyl alcohol, cetyl palmitate, hard fat, coconut oil and arachis oil; and said gel former being selected from the group consisting of xanthan, alginic acid, alkali metal alginate, gum arabic, agar, ghatti gum, karaya gum, tragacanth, guar gum, locust bean gum, pectin, chitin, amylopectin, gelatin, hydroxymethylpropylcellulose, methylcellulose, hydroxypropylcellulose, hydroxyethylcellulose, ethylcellulose, sodium carboxymethylcellulose, sodium carboxyethylcellulose, montmorillonite, polyacrylic acid, methyl ester of polyacrylic acid, ethyl ester of polyacrylic acid, sodium carboxymethyl starch and sodium carboxyethylstarch.

2. A solid oral administration form according to claim 1, wherein said extraction-preventing composition comprises said surfactant and said fat or gel former in a weight ratio of from 5-60:40-90.

3. A solid oral administration dosage form according to claim 2, wherein upon extraction with organic solvent no more than 25 percent of said active ingredient is contained in said organic solvent.

4. A solid oral administration form according to claim 2, wherein said extraction-preventing composition is blended with said pharmacologically active ingredient in an amount of 10-150:1.

5. A solid oral administration dosage form according to claim 4, wherein upon extraction with organic solvent no more than 8 percent of said active ingredient is contained in said organic solvent.

6. A solid oral administration form according to claim 4, wherein said extraction-preventing composition comprises said surfactant and said fat or gel former in a weight ratio of from 20-60:40-80.

7. A solid oral administration dosage form according to claim 6, wherein upon extraction with organic solvent no more than 4 percent of said active ingredient is contained in said organic solvent.

8. A solid oral administration form according to claim 6, wherein said extraction-preventing composition is blended with said pharmacologically active ingredient in an amount of 20-100:1.

9. A solid oral administration dosage form according to claim 8, wherein upon extraction with organic solvent no more than 2 percent of said active ingredient is contained in said organic solvent.

10. A solid oral administration form as claimed in any one of claims 1–9, which comprises racemic ephedrine.

11. A solid oral administration form as claimed in any one of claims 1–9, which comprises (+)-ephedrine.

12. A solid oral administration form as claimed in any one of claims 1–9, which comprises (−)-ephedrine.

13. A solid oral administration form as claimed in any one of claims 1–9, which comprises racemic pseudoephedrine.

14. A solid oral administration form as claimed in any one of claims 1–9, which comprises (+)-pseudoephedrine.

15. A solid oral administration form as claimed in any one of claims 1–9, which comprises (−)-pseudoephedrine.

16. A solid oral administration form as claimed in any one of claims 1–9, which comprises norephedrine.

17. A solid oral administration form as claimed in any one of claims 1–9, which comprises norpseudoephedrine.

* * * * *